United States Patent [19]

Reese et al.

[11] Patent Number: 5,019,511

[45] Date of Patent: May 28, 1991

[54] **ERYTHROCYTIC MEMBRANE ANTIGENS OF *P. FALCIPARUM*-INFECTED ERYTHROCYTES**

[76] Inventors: Robert T. Reese, 10886 Aviary Ct., San Diego, Calif. 92131; Harold A. Stanley, 8689 Via Mallorca, La Jolla, Calif. 92037

[21] Appl. No.: 183,456

[22] Filed: Apr. 14, 1988

Related U.S. Application Data

[63] Continuation of Ser. No. 891,752, Jul. 31, 1986.

[51] Int. Cl.$^5$ ................... C12N 5/00; A61K 35/14; C07K 3/00; C07K 13/00
[52] U.S. Cl. ..................... 435/240.27; 530/387; 530/809
[58] Field of Search .................. 530/387, 809; 435/240.26, 240.27

[56] References Cited

U.S. PATENT DOCUMENTS 4,632,909 12/1986 Carter ................................. 424/85

FOREIGN PATENT DOCUMENTS 8503724 8/1985 United Kingdom

OTHER PUBLICATIONS

Oldrink et al, FEBS 1984, p. 108 vol. 173.
Lyon et al, PNAS vol. 83, 1986 pp. 2989–2993.
Holder et al, *Nature* 317, 1985, pp. 270–273.
Santoro et al, *WBC* 258, 1983, p. 334.
Stanley et al., *Proc. Natl. Acad. Sci. USA*, 83:6093–6097 (1986).
Howard et al,, *Mol. Biochem. Parasitol.*, 17:61–77 (1985).
Stanley et al., *Mol. Biochem. Parasitol.*, 36:139–150 (1989).
Howard et al., *Gene*, 46:197–205 (1986).
E. Nardin et al., *Nature*, 274, 55–57 (1978).
H. Stanley et al., *J. Immunol.*, 134, 3439–3444 (1985).
F. Ardeshir et al., *Proc. Nat'l Acad. Sci.*, 82, 2518–2522 (1985).
W. Trager et al., *Bull. World Health Org.*, 35, 883–885 (1966).
S. G. Langreth et al., *J. Exp. Med.*, 150, 1241–1254 (1979).
H. A. Stanley et al., *J. Molec. Immunol.*, 21, 145–150 (1984).
H. A. Stanley et al., *Am. J. Trop. Med. Hyg.*, 33, 12–16 (1984).
I. J. Udeinya et al., *Nature*, 303, 429–431 (1983).
A. Kilejian, *Proc. Nat'l Acad. Sci. USA*, 76, 4650–4653 (1979).
A. Kilejian, *J. Exp. Med.*, 151, 1534–1538 (1980).
R. L. Coppel et al., *Nature*, 310, 789–792 (1984).
H. Perlmann et al., *J. Exp. Med.*, 159, 1686–1704 (1984).
G. V. Brown et al., *J. Exp. Med.*, 162, 774–779 (1985).
J. Gruenberg et al., *Proc. Nat'l Acad. Sci. USA*, 80, 1087–1091 (1983).
J. H. Leech et al., *J. Exp. Med.*, 159, 1567–1575 (1984).
S. B. Aley et al, *J. Exp. Med.*, 160, 1585–1590 (1984).
S. B. Aley et al., *Parasitology*, 92, 511–525 (1986).
B. S. Jacobsen et al., *Science*, 195, 302–304 (1977).
Holder and Freeman, *J. Exp. Med.*, 160, 624–629 (1984).
Simmons et al., *EMBO J.*, 6, 485–491 (1987).
H. Stanley et al., *J. Immunol.*, 134, 3439–3444 (1985).
Vermuillen, A. N. et al, 1985, Develop. Biolog. Standard, vol. 62, pp. 91–97, "*Plasmodium falciparum* Transmission Blocking . . . ".
Vermeullen, A. N. et al, 1985, J. Exp. Med. 162:1460–1476, "Sequential Expression of Antigens on Sexual Stages of Plasmodium . . . ".

*Primary Examiner*—Margaret Moskowitz
*Assistant Examiner*—Thomas Cunningham
*Attorney, Agent, or Firm*—Dressler, Goldsmith, Shore, Sutker & Milnamow, Ltd.

[57] ABSTRACT

Monoclonal antibodies are disclosed that react with an antigenic polypeptide having a molecular weight of approximately 45,000 that is expressed in the cell membrane of *P. falciparun*-infected erythrocytes. The antibodies were raised using the Honduras CDC isolate, and can be used for diagnostic purposes. The hybridoma producing the monoclonal antibodies is also disclosed.

2 Claims, No Drawings

ERYTHROCYTIC MEMBRANE ANTIGENS OF *P. FALCIPARUM*-INFECTED ERYTHROCYTES

This invention was made with government support under Grant DPE-0453-C-00-1017-00 awarded by the Agency for International Development. The government has certain rights in this invention.

This is a continuation of co-pending application Ser. No. 891,752 filed on July 31, 1986.

This invention relates to certain antigenic polypeptides associated with the membrane of erythrocytes infected with *Plasmodium falciparum*, in particular, polypeptides of approximate molecular weights 20,000, 35,000, 45,000 and 55,000. The invention also relates to monoclonal antibodies specific to the polypeptides. The invention further relates to the use of the polypeptides as vaccines.

Malaria is caused by parasites of the genus Plasmodium, with *Plasmodium falciparum* being a form of the parasite of particular concern to humans. The *P. falciparum* parasite, which is mosquito-borne, is introduced into the body in the sporozoite form. The sporozoite travels to the liver where it is converted into the merozoite form of the parasite. Merozoites, upon release from the liver into the blood stream, attack and invade red blood cells (erythrocytes). Inside the erythrocyte, the parasite undergoes a complex developmental cycle of approximately 48 hours duration. During this cycle the parasite goes through a ring stage (lasting approximately 20 hours), a trophozoite stage (lasting approximately 20 hours) and a schizont stage (lasting approximately 8 hours). The final maturation of the parasite results in the release of 10 to 30 merozoites from the erythrocyte, each of which is capable of invading a new erythrocyte and initiating a new cycle of intracellular (intraerythrocytic) development. As used herein the term "red blood cell stage parasite" or "erythrocytic stage parasite" shall be taken to embrace each of the various intraerythrocytic stages of the parasite.

There have been a number of reports of antigenic polypeptides on the surface of *P. falciparum* in its various stages. There have also been reports of corresponding antibodies, including monoclonal antibodies, to such polypeptides as well as reports of the possibilities for using such polypeptides in vaccines.

There have been reports of antigenic *P. falciparum* sporozoite surface polypeptides and their possible use as vaccines. There have also been reports of antigenic *P. falciparum* merozoite surface polypeptides and their possible use as vaccines. E. Nardin et al., *Nature*, 274, 55-57 (1978); H. Stanley et al., *J. Immunol.*, 134, 3439-3444 (1985); F. Ardeshir et al., *Proc. Nat'l Acad. Sci.*, 82, 2518-2522 (1985).

In addition, there have been reports of changes in the nature and composition of the erythrocyte plasma membrane (the plasma membrane is the outer cell membrane; it will be referred to herein on occasion as the "cell membrane" or the "membrane") of parasitized erythrocytes. Specifically, during the development of ring stages into trophozoite stages, several changes occur in the host cell plasma membrane. An obvious structural change, visualized by electron microscopy, is the appearance of electron-dense structures, referred to as knobs, under the lipid bilayer the erythrocyte membrane: W. Trager et al., *Bull. World Health Org.*, 35, 883-885 (1966).

Coincidental with the appearance of knobs, the erythrocyte cell membrane changes antigenically such that antibodies from immune sera can bind to the infected red blood cell surface; S. G. Langreth et al., *J. Exp. Med.*, 150, 1241-1254 (1979). The presence of antigenic sites on the parasitized erythrocytic membrane, and the possibility of binding of antibodies to these sites, is important in several respects. First, the binding of antibodies can activate the classical complement pathway and augment the alternative complement pathway, thus leading to the deposition of biologically reactive complement components; H. A. Stanley et al., *J. Molec. Immunol*, 21, 145-150 (1984). Second, the binding of antibodies can inhibit the uptake by the erythrocyte of various nutrients and thereby inhibit the intracellular growth of the parasite; H. A. Stanley et al., *Am. J. Trop. Med. Hyg.*, 33, 12-16 (1984). Third, there is evidence that, at least in vitro, the binding of antibodies can result in a dissociation of infected red blood cells from endothelial cells I. J. Udeinya et al., *Nature*, 303, 429-431 (1983). A consequence of this, in vivo, would be the circulation of late-stage infected erythrocytes and the possibility of removal from circulation by splenic cells.

Knowledge of the identity of antigenic polypeptides in the parasitized erythrocyte would provide a basis for developing antibodies and vaccines useful in controlling malaria. To date, however, little has been reported on the characteristics or identity of such polypeptides and, in particular, the antigenic composition of the erythrocytic membrane has not been well characterized.

There has been work disclosing a histidine-rich molecule of approximate molecular weight 80,000-95,000 (80K-95K), reported as being part of the parasite-derived, electron-dense material of the knob on the erythrocyte membrane; A. Kilejian, *Proc. Natl. Acad. Sci. U.S.A.*, 76, 4650-4653 (1979); A. Kilejian, *J. Exp. Med.*, 151, 1534-1538 (1980).

There have also been reports that a polypeptide of relative molecular weight ($M_r$) 155K which is made during schizogony (asexual nuclear division) is inserted into the erythrocyte membrane during merozoite invasion; R. L. Coppel et al., *Nature*, 310, 789-792 (1984); H. Perlmann et al., *J. Exp. Med.*, 159, 1686-1704 (1984). It has been reported that this polypeptide species resolved into a closely migrating doublet. G. V. Brown et al., *J. Exp. Med.*, 162, 774-779 (1985); H. Perlmann et al., *J. Exp. Med.*, 159, 1686-1704 (1984).

In addition there have been reports of larger molecular weight polypeptides in the parasitized erythrocyte. It has been reported that an over-200K molecular weight antigen, obtained using a membrane purification procedure, was present in both knobby and knobless isolates; J. Gruenberg et al., *Proc. Natl. Acad. Sci. U.S.A.*, 80, 1087-1091 (1983). There has also been a report of work in which surface iodination of infected erythrocytes was used to characterize a polypeptide, the molecular weight of which varied between two isolates (260K vs. 285K); J. H. Leech et al. *J. Exp. Med.*, 159, 1567-1575 (1984). Another report stated that this antigen was not present in knobless isolates; S. B. Aley et al., *J. Exp. Med.*, 160, 1585-1590 (1984).

Accordingly, there has been a need for the identification and isolation of antigenic polypeptides on the surface of membranes of the erythrocytes parasitized by *P. falciparum*.

In accordance with the invention novel antigenic polypeptides associated with polypeptides on the surface of erythrocytes parasitized with *P. falciparum* have been identified, characterized and isolated.

The invention embraces novel, antigenic polypeptides of approximate molecular weights 20,000, 35,000, 45,000 and 55,000 (20K, 35K, 45K and 55K) which correspond to membrane polypeptides, in particular polypeptides on the surface of the membrane, of erythrocytes parasitized with *P. falciparum*. The invention also embraces a novel, antigenic erythrocytic membrane polypeptide of approximate molecular weight 120,000. The invention is particularly directed to these polypeptides as found in erythrocytes containing parasites which have advanced to the trophozoite or schizont stage. The polypeptides of the invention include polypeptides derived from the infected erythrocytes and polypeptides which are otherwise substantially similar to polypeptides derivable from the infected erythrocytes. Preferred sources of the polypeptide include the *P. falciparum* isolates Honduras I CDC, FVO, Indochina I, and Tanzania.

The invention further embraces antigenic polypeptide fragments of the 20K, 35K, 45K and 55K polypeptides which substantially retain the antigenic properties of the respective parent polypeptides (as used in this context, the term "fragment" embraces such fragments modified by the addition of other molecular parts to create a larger molecule which substantially retains the antigenic properties of the fragment).

The polypeptides of the invention are preferably derived from human erythrocytes grown in cell culture. The invention embraces the polypeptides in chemically pure form. The invention also embraces vaccines and vaccine compositions comprising one or more of the polypeptides of the invention.

The invention further embraces hybridoma cell lines HB9153 and HB9152 which produce monoclonal antibodies specific to, respectively, the 20K and 45K polypeptides. The invention also embraces monoclonal antibodies which are produced, respectively, by hybridoma cell lines HB9153 and HB9152, and which are specific to, respectively, the 20K and 45K polypeptides.

The invention additionally embraces a method of isolating the antigenic polypeptides of the invention. The method comprises isolating erythrocytes parasitized with *P. falciparum*, preferably at the trophozoite or schizont stage; isolating the protein fraction from the erythrocytes, preferably by binding the erythrocytes to a support, with poly-L-lysine being a preferred binding agent, so as to create a monolayer of erythrocytes, and then lysing the erythrocytes to permit polypeptide isolation; and isolating the desired polypeptide using known physical methods of fractionation such as electrophoresis. This approach is advantageous in that the highly charged poly-lysine distorts the cells due to its strong attraction for the erythrocyte membrane. This causes most of the available space to be covered with cells leaving few gaps among them. In addition, the strong adhesion of the membrane to the poly-lysine coated plate and the distortion of the cell which it causes increases the fragility of the parasitized erythrocyte making it easier to lyse. In the case of the 20K or 45K polypeptides, the polypeptides are preferably identified and isolated using the monoclonal antibodies of the invention.

The invention further embraces a method of immunizing a host to confer protective immunity against malaria caused by *P. falciparum*. The method comprises inoculating the host with a vaccine or a vaccine composition comprising one or more of the polypeptides of the invention, or fragments thereof.

The novel polypeptides of the invention are isolated from erythrocytes infected with *P. falciparum*. A variety of strains or isolates of *P. falciparum* can be used to infect the erythrocytes, including isolates Honduras I CDC, FVO, Indochina I and Tanzania. The results reported in Example 7 show that other isolates as well give rise to antibodies to the polypeptides of the invention.

Infected erythrocytes to be used as the source of polypeptides may contain parasites at various points of the intraerythrocytic development cycle, with trophozoite-stage parasites being preferred. Erythrocyte cells are preferably of human origin. Cells may be parasitized and grown in culture using known methods. See Example 1.

To obtain the polypeptides from parasitized erythrocytes, the erythrocytic membranes are preferably isolated from whole cells in a separate step. A preferred method of membrane isolation is to bind the erythrocytes to a solid surface (e.g., to the inside surface of a flask coated with poly-L-lysine), preferably in a monolayer. The bound whole cells are disrupted, e.g., by shaking with glass beads, and protein remaining bound is removed by application of an appropriate solution.

Particular polypeptides of the invention may be isolated from the protein fraction in ways known in the art. For instance, the polypeptides may be resolved on a polyacrylamide gel containing SDS and selection made based on molecular weight. See Example 2. Individual polypeptides may be obtained directly from the gel. One approach is to immunoprecipitate individual polypeptides from membrane preparations with human or monkey antisera which contain the appropriate antibodies. This is best achieved by binding the antibodies to an insoluble support, dissociating the bound antigens, and then separating the antigens by SDS polyacrylamide gel electrophoresis.

A preferred method of identifying and isolating the 20K and 45K polypeptides of the invention is to use the respective monoclonal antibodies of the invention, in ways known in the art. A preferred approach is to immobilize monoclonal antibodies on a solid support and to use affinity chromatography techniques.

The polypeptides of the invention may be derived from erythrocytic membranes (as described above) or produced synthetically, e.g., by recombinant DNA techniques. The invention also embraces modifications or fragments of the polypeptides, where such modifications or fragments retain substantially the antigenic characteristics of the parent polypeptides.

The hybridoma cell lines of the invention (ATCC numbers HB9153 and HB9152) were produced using known methods. Mice were injected with a mixture of trophozoites and schizonts. Mouse splenocytes were fused to mouse myelomas. Supernatants from the resultant hybridomas were screened for the presence of monoclonal antibodies specific to the polypeptides of the invention using the indirect immunofluorescence technique on parasitized erythrocytes. See Example 6. The fact that monoclonal antibodies specific to these polypeptides could be produced in this manner showed the antigenicity of the polypeptides.

Polypeptides of the invention were shown to be present in the membranes of parasitized erythrocytic cells, and not in the membranes of non-parasitized erythrocytic cells, by comparison of electrophoresis gels with silver staining. This comparison showed a number of polypeptides which were present only in the membranes of parasitized cells, including the 35K, 45K and 55K polypeptides. The 20K polypeptide was not singled out in this experiment because uninfected erythrocytes also have a membrane polypeptide of comparable molecular weight. See Example 3.

Polypeptides of the invention were shown to be parasite-derived, as opposed to being erythrocyte polypeptides modified by parasitization, in a separate experiment. Membranes isolated from infected erythrocytes were metabolically labeled with $^{35}$S-methionine (hereinafter 35-S-methionine). The cells were labeled from ring stage through trophozoite stage. The 55K, 35K and 20K polypeptides displayed detectable label. A similar labeling of uninfected cells showed no detectable incorporation of 35-S-methionine polypeptides. See Example 4.

Another experiment was conducted to identify polypeptides exposed in whole or part on the surface of erythrocytes. Uninfected and trophozoite-infected intact erythrocytes were surface-labeled by lactoperoxidase iodination, and the labeled polypeptides were compared by SDS polyacrylamide gel electrophoresis. Polypeptides of molecular weight 20K, 35K, 45K and 55K were identified in the infected erythrocytes and not in the uninfected erythrocytes. See Example 5.

Table I below provides a summary of evidence obtained in the three above-described experiments concerning the polypeptides of the invention ("+" means evidence of polypeptide; "−" means no evidence of polypeptide). The silver stain experiment was with a membrane preparation; the metabolic label experiment (ring stage to trophozoite stage with 35-S-methionine) was with a membrane preparation; and the iodination experiment was with intact cells. See Examples 3-5 for further information on these experiments.

TABLE I

| Molecular Weight | Silver Stain | Metabolic Label | Iodination |
| --- | --- | --- | --- |
| 55K | + | + | + |
| 45K | + | − | + |
| 35K | + | + | + |
| 20K | − | + | + |

An additional experiment was conducted to show the reactivity of human sera with the polypeptides of the invention. A series of Nigerian sera was shown to contain antibodies to antigens corresponding to polypeptides of approximate molecular weight 20K, 35K, 45K and 55K. See Example 7. This demonstrated not only that humans have the genetic capacity to respond to these antigens but also that individuals who are at least partially immune contain antibodies against them, suggestive of their role in immunity.

The polypeptides of the invention, individually or in combination, may be used in vaccines in ways known in the art. The method of presentation, including choice of adjuvant or carrier (e.g., binding to potassium alum), is based on optimal immune response to each antigen.

The polypeptides of the invention may also be used as a means to produce antibodies, polyclonal or monoclonal, for diagnostic or therapeutic use in treatment of P. falciparum-caused malaria.

EXAMPLES

Example 1

Source and Preparation of Parasites

The Honduras I CDC (K+) isolate of Plasmodium falciparum was used in most of the experiments; FVO, Indochina I and Tanzania isolates were used where indicated. The parasites were grown by the method of Trager and Jenson; W. Trager et al., Science, 193, 673–675 (1976). The parasites were synchronized by sorbitol treatment; C. Lambros et al., J. Parasitol., 65, 418–420 (1980). To obtain infected erythrocytes for the membrane isolations (Example 2) and iodination experiments (Example 5), the trophozoite-infected erythrocytes were concentrated by Physiogel separation; R. T. Reese et al., Bull. World Health Org., 57 (Suppl. 1), 53–61 (1979). Uninfected erythrocytes, used as controls, were similarly kept in culture and treated with Physiogel.

Membrane isolations were also done using metabolically labeled cells (see Example 4). In these experiments, the trophozoites were first concentrated by Physiogel treatment and then placed back into culture at a 3% parasitemia. After merozoites had formed and reinvasion had occurred, the erythrocytes (15–20% parasitemia with ring-stage parasites) were washed once with RPMI-1640 medium and placed into culture at 1% hematocrit using methionine-free RPMI-1640 medium supplemented with 25 mM HEPES, 10% (v/v) human serum, and 0.1 mCi/ml 35-S-methionine (Amersham). After approximately 18 hours in culture, during which time the ring-stage parasites matured into trophozoites, the erythrocytes were washed with RPMI-1640 and used for membrane isolations. In these experiments, the trophozoite-infected erythrocytes were not concentrated by Physiogel treatment.

Example 2

Membrane Isolation and Polypeptide Fraction Isolation

Membrane isolations were done using T-25 flasks (Corning) previously left overnight with 5 ml of 0.2 mg/ml poly-L-lysine (approximately 14,000 molecular weight, Sigma) in 5% (w/v) sodium bicarbonate. Both the cells used in the membrane isolations and the flasks were washed twice with 10 mM PBS pH 7.4. The cells were diluted to a 5% hematocrit with PBS, and 3–4 ml aliquots were added to each flask. The cells were allowed to settle for 10–20 minutes at room temperature, and unbound cells were removed by washing twice with PBS. This resulted in a monolayer of erythrocytes coating the bottom of the flasks. Ten milliliters of PBS containing 2 ml of glass beads (0.5 mm diameter, Thomas Scientific) were then added, and the flasks were vigorously shaken. The glass beads and cellular fragments were removed by three washes with PBS. In one set of flasks, the cells were fixed with 2% glutaraldehyde in 0.1M cacodylic buffer and 0.12M sucrose either before or after cellular disruption. The intact cells or residual membranes were then processed for scanning electron microscopy (SEM). Shaking the cells with glass beads disrupted the erythrocytes such that, after washing with PBS, no intact parasites or infected erythrocytes could be seen attached to the flasks. The membrane fraction (including the polypeptide fraction) bound to the flask was removed with Laemmli SDS sample buffer (0–0.5 ml/flask).

To control for the "nonspecific" binding of intracellular parasite proteins during the disruption of the erythrocytes with glass beads, infected red blood cells were first lysed by freezing and thawing, and the total lysate was placed into poly-lysine-coated flasks. Analysis showed some residual nonspecific binding due to intracellular proteins having a high affinity for the poly-lysine-coated flasks. Attempts to block such "nonspecific" binding by treating the flasks with dextran sulfate or heparin sulfate prior to cellular disruption were not successful because: 1) the treatments weakened the binding of the erythrocytes to the plates so that membrane fragments (indicated by the presence of spectrin) were not obtained; and, 2) the "nonspecific" binding also occurred using flasks which had not been pretreated with polysine. The lower of the two parasite bonds at 35K (mentioned in Example 3) was shown to be due to nonspecific binding.

Example 3

SDS-PAGE Silver Stain Analysis

The polypeptide fractions removed from each flask (50 ul aliquots as described in Example 2 above were resolved on 6-14% gradient polyacrylamide gels containing SDS with 3% stacking gels. The molecular weight markers used in the various gels were: myosin (250K), beta-galactosidase (116K), phosphorolase-beta (97K), bovine serum albumin (69K), gamma-globulin heavy chain (53K), ovalbumin (43K), carbonic anhydrase (29K), and betalactoglobulin (18K). The gels were then silver stained, J. H. Morrissey, *Anal. Biochem.*, 117, 307-310 (1981); and processed for fluorography, W. M. Bonner et al., *Eur. J. Biochem.* 10, 1766-1771 (1970).

Analysis of results of polyacrylamide gel electrophoresis of the polypeptides remaining bound to the flasks, as compared to results when uninfected erythrocytes were used for the membrane preparations, showed that a number of polypeptides appeared to be specific for the infected erythrocytes. The most prominent of these had molecular weights of greater than 240K (an exact molecular weight was not assigned since no marker having a molecular weight greater than the 240k spectrin was available), 150K, 120K, and 35K. The proteins migrating at 150K and 35K appeared as doublets. Less intense bands were also observed at 55K and 45K. Detection by silver staining showed that these antigens were present in substantial amounts.

Example 4

Metabolic Labelling

To determine which polypeptides were parasite-derived polypeptides, as opposed to modified erythrocyte polypeptides, membranes were isolated from infected (Honduras I CDC) red blood cells metabolically labeled with 35-S-methionine as described in Example 1. The cells were labeled from ring stage through trophozoite stage. A similar labeling of uninfected erythrocytes showed no detectable incorporation of 35-S-methionine into erythrocyte proteins. Experimental results with infected erythrocytes showed labeling with at least four antigens: over 240K, 55K, 35K (weak), and approximately 20K. Nearly identical results were obtained using three other isolates from various parts of the world: FVO (K+ and K− clones produced by limiting dilution), Indochina I (K−), and Tanzania (K+). The only difference in results may be that the molecular weight of the over 240K polypeptide was distinctly different in the various isolates.

Example 5

Surface Iodination

To identify parasite proteins of which parts were exposed on the surface of red blood cells, Physiogel-treated trophozoites and uninfected erythrocytes were iodinated by a modified lactoperoxidase method; D. R. Phillips et al., *Biochem.*, 10, 1766-1771 (1970). In these experiments, 150ul aliquots of packed cells were resuspended to a 10% packed cell volume in RPM1-1640 containing $10^{-6}$M KI, 0.25 mg lactoperoxidase (Sigma), and 0.3 mCi $^{125}$I (Amersham). Hydrogen peroxide (0.03%) was then added: 5 ul at time 0, 2 ul at 1 minute and again at 2 minutes, 1 ul at 3 minutes and 4 minutes. Before adding the $H_2O_2$ at 1 minute and 3 minutes, 0.5 mls of the cell suspensions were removed and diluted in 5 ml 1% BSA/5 mM KI/RPM1-1640. The remaining 0.5 ml aliquot was similarly diluted at 5 minutes. The cells were then washed once with 15 ml 1% BSA in RPM1-1640 and once with RPM1-1640. The pellets were solubilized in SDS sample buffer, and the proteins from equivalent volumes of cells were resolved on 6-14% gradient polyacrylamide gels containing SDS using 3% stacking gels.

The major protein labeled in infected and uninfected red blood cells had a molecular weight of approximately 85K. Several other polypeptides, labeled to a lesser degree, were also observed from infected and uninfected cells. Spectrin was not detectably labeled in these experiments. Polypeptides of 35K, 45K and 55K were identified in the infected red blood cells and not from the uninfected erythrocytes. A longer exposure of the gel allowed better visualization of an approximately 20K polypeptide specific for infected erythrocytes.

Example 6

Hybridoma Preparation and Monoclonal Antibody Selection

Mice were injected intraperitoneally with 0.1 ml of a 50% suspension of frozen and thawed erythrocytes, half of which were infected with trophozoite-, schizont-, or segmenter-stage Honduras CDC isolate *P. falciparum* parasites. Two months later, the animals were boosted with a second 0.1 ml aliquot of the same material. Three days later, splenic cells were harvested from two mice and pooled. Two-thirds of these cells were frozen, half of which were to be used in fusion 30, the fusion from which these hybridomas were obtained. To produce the hybridomas, one vial of $5-10 \times 10^6$ cells was rapidly thawed at 37° C., washed twice with Dulbecco's high-glucose medium and mixed with an equal number of similarly washed P3X63 Ag8.653 myelomas. The cells were then pelleted by centrifugation for 10 min at $1300 \times g$. After removing the supernatant, the pellet was gently loosened. One milliliter of 37° C. fusion promoter (35% PEG 1000 and 7.5% dimethyl sulfoxide in RPMI 1640) was slowly added over a 1-min time interval. Warm Dulbecco's medium containing 10% gamma-globulin-free horse serum was then slowly added, 2 ml in a 2-min interval followed by 8 ml in 2 min. After centrifugation for 10 min at $1300 \times g$, the fused cells were diluted to the appropriate cell density in Dulbecco's high-glucose medium containing 10% gamma-globulin-free horse serum, hypoxanthine (14 ug/ml), aminopterin (0.45 ug/ml), and thymidine (7.2 ug/ml)

(HAT medium) and dispensed in 96-well plates. BALB/c ByJ mouse thymocytes ($2 \times 10^6$/ml) were used as a feeder layer. The cultures were fed weekly with HAT medium supplemented on days 7 and 15 with fresh thymocytes. The hybridoma culture supernatants were screened by IFAT using a fluorescein isothiocyanate conjugate of affinity-purified goat antimouse IgG and IgM antibodies (Tago, Burlingame, Calif.). Hybridoma cell line F30 P4 6D (deposited with the American Type Culture Collection in Rockville, Md. as ATCC number HB9153) producing antibodies against the 20,000 molecular weight antigen and hybridoma cell line F30 P8 3B (deposited with the American Type Culture Collection in Rockville, Md. as ATCC number HB9152) producing antibodies against the 45,000 molecular weight antigen were isolated and then cloned by limiting dilution.

Example 7

Reactivity With Human Sera

A series of 20 Nigerian sera were tested using Western immunoblots for their reactivity with polypeptides associated with parasitized erythrocyte membranes. Membranes were isolated as described above, solubilized in buffer for SDS PAGE, and the polypeptides separated electrophoretically. Immunoblots were conducted using the immune human sera and $^{125}$I-labeled rabbit antihuman immunoglobulin according to known procedures; F. Ardeshir et al., *Proc. Natl. Acad. Sci. U.S.A.*, 82, 2518-2522 (1985). Although different sera had reactivity with different subsets of parasite polypeptides, as a whole the sera contained antibodies to polypeptides of approximate molecular weights 270-350K, 150K, 120K, 55K, 45K, 35K and 20K. The results evidenced the antigenicity of the listed polypeptides. Of these, the 120K, 55K, 45K, 35K and 20K polypeptides correspond to the polypeptides of the invention.

What is claimed is:

1. Hybridoma cell line ATCC HB 9152 which produces a monoclonal antibody that specifically binds to a polypeptide of approximate molecular weight 45,000 present in the membrane of erythrocytes parasitized with *P. falciparum* and not present in the membrane of non-parasitized erythrocytes.

2. The monoclonal antibody produced by hybridoma cell ATCC HB9152, which specifically binds to a polypeptide of approximate molecular weight 45,000 present in the membrane of erythrocytes parasitized with *P. falciparum* and not present in the membrane of non-parasitized erythrocytes.

* * * * *